(12) United States Patent
Bowden et al.

(10) Patent No.: US 6,806,388 B2
(45) Date of Patent: Oct. 19, 2004

(54) POLYFLUORINATED AROMATIC OR HETEROCYCLIC DERIVATIVES WITH SULPHURPENTALFLUORIDE GROUP(S)

(75) Inventors: Roy Dennis Bowden, Lea Town (GB); Martin Paul Greenhall, Lea Town (GB)

(73) Assignee: F2 Chemicals Limited, Preston (GB)

( * ) Notice: Subject to any disclaimer, the term of this patent is extended or adjusted under 35 U.S.C. 154(b) by 0 days.

(21) Appl. No.: 10/181,063

(22) PCT Filed: Nov. 23, 2001

(86) PCT No.: PCT/GB01/05165
§ 371 (c)(1),
(2), (4) Date: Nov. 15, 2002

(87) PCT Pub. No.: WO02/42263
PCT Pub. Date: May 30, 2002

(65) Prior Publication Data
US 2003/0096999 A1 May 22, 2003

(30) Foreign Application Priority Data
Nov. 25, 2000 (GB) .............................. 0028797

(51) Int. Cl.[7] .............................................. C07C 323/09
(52) U.S. Cl. ....................... 568/74; 568/936; 568/937; 564/404; 564/440; 514/646; 514/706
(58) Field of Search ......................... 568/74, 936, 937; 564/404, 440

(56) References Cited

U.S. PATENT DOCUMENTS 3,073,861 A * 1/1963 Raasch ........................ 260/552
3,117,158 A * 1/1964 Sheppard ..................... 260/543

FOREIGN PATENT DOCUMENTS

| GB | WO9422817 | 10/1994 |
| GB | WO9705106 | 2/1997 |

OTHER PUBLICATIONS

Database CAPLUS on STN, Acc. No. 1999:613599, Chern et al., Sep. 23, 1999, WO 9947073 (abstract).*
Database CAPLUS on STN, Acc. No. 1999:613663, Chern et al., Sep. 23, 1999, WO 9947139 (abstract).*
Database Registry Online; Chemical Abstracts Service, RN=1766–46–7, 1546–66–3 & 736–97–0, XP002190620.

* cited by examiner

Primary Examiner—Brian Davis
(74) Attorney, Agent, or Firm—Crowell & Moring LLP

(57) ABSTRACT

The invention provides polyfluorinated aromatic or heterocyclic compounds comprising at least three ring substituents, at least one of which comprises a sulfurpentafluoride group and at least one of which comprises a labile group; methods for their preparation are also disclosed. Preferably, the compounds comprise either two sulfurpentafluoride groups or one sulfurpentafluoride group and one other polyfluorinated group, such as a trifluoromethyl group. Said labile group preferably comprises an amino, bromo or nitro group. Said compounds are useful in the preparation of medicaments.

12 Claims, No Drawings

POLYFLUORINATED AROMATIC OR HETEROCYCLIC DERIVATIVES WITH SULPHURPENTALFLUORIDE GROUP(S)

This application is a 371 of PCT/GB01/05165 filed Nov. 23, 2001.

This invention relates to polyfluorinated aromatic and heterocyclic compounds and methods for their production; specifically, the invention is concerned with compounds which contain sulphurpentafluoride groups.

The preparation and use of various polyfluorinated aromatic and heterocyclic derivatives is well documented in the prior art, and the compounds in question have found widespread use, for example as intermediates in the pharmaceutical industry. Of particular value in this connection are intermediates containing trifluoromethyl groups, especially trifluoromethylbenzene derivatives; a favored end-group in this context is a 3,5-bis(trifluoromethyl)phenyl group which has been developed for use in a range of anti-asthma and anti-arthritis drugs. Such a group may be introduced into a drug molecule by means of a suitable labile group in the 1-position so that, for example, 3,5-bis(trifluoromethyl) bromobenzene is a useful intermediate for the preparation of such drugs.

The present inventors have now found that alternative polyfluorinated derivatives may be obtained by relatively straightforward synthetic procedures to provide a further range of intermediates with potentially widespread industrial applicability, particularly in relation to pharmaceuticals.

Various organic sulphur pentafluorides, and methods for their preparation, have previously been disclosed in PCT Patent Application WO 97/05106. The present inventors have now found that specific derivatives of this type are of particular value in the synthesis of pharmaceuticals; such derivatives comprise trisubstituted compounds comprising at least one sulphur pentafluoride group and at least one labile group.

Thus, according to a first aspect of the present invention, there is provided a polyfluorinated aromatic or heterocyclic compound comprising at least three ring substituents, at least one of which comprises a sulfurpentafluoride group and at least one of which comprises labile group.

Said aromatic or heterocyclic compound may be based on any suitable ring system, but particularly favorable results may be obtained with compounds based on aromatic ring systems such as benzene, naphthalene, anthracene or phenanthrene, with benzene derivates being especially preferred. Of particular value are trisubstituted benzene derivates, substituted in the 1-, 3- and 5-positions.

Said polyfluorinated aromatic or heterocyclic compound comprising at least three ring substituents, at least one of which comprises a sulfurpentafluoride group and at least one of which comprises a labile group preferably includes one or two sulfurpentafluoride groups. Compounds which comprises only one sulfurpentafluoride group typically also comprise a further fluorinated group, preferably a trifluoromethyl group.

The labile group comprises a substituent capable of facilitating further reaction with another compound during, for example, drug production. Suitable reactive groups in the content of the compounds of the present invention are groups which are labile as a result of the powerful electron-withdrawing inductive effect of the polyfluorinated groups in the molecule, typical examples being amino, bromo and nitro groups.

Specifically preferred compounds according to the present invention are (3-amino-5-trifluoromethyl)phenyl) sulfurpentafluoride, (3-bromo-5-trifluoromethyl)phenyl) sulfurpentafluoride, (3-nitro-5-trifluoromethyl)phenyl) sulfurpentafluoride, 3,5-bis(pentafluorosulfuryl)aniline 3,5-bis(pentafluorosulfuryl)bromobenzene and 3,5-bis (pentafluorosulfuryl)nitrobenzene.

The present invention also envisages methods applicable to the preparation of the compounds of the first aspect of the present invention. Thus, according to a second aspect of the present invention, there is provided a method of preparation of a polyfluorinated aromatic or heterocyclic compound comprising at least three ring substituents, at least one of which comprises a sulfurpentafluoride group and at least one of which comprises a labile group, said method comprising:

(a) treating an aromatic or heterocyclic compound comprising at least two ring substituents, at least one of which comprises a disulfide or thiol group, with fluoride; and (b) introducing a labile group into said fluorinated precursor.

Preferably, said treatment with fluorine is carried out using gaseous elemental fluorine.

Thus, for example, bis(3-trifluoromethyl)disulfide has been fluorinated by treatment with elemental fluorine to give 3-(trifluoromethyl)phenyl sulfurpentafluoride and, in a similar fashion, 1,3-bis(pentafluorosulfuryl)benzene has been obtained from the direct fluorination of benzene-1,3-dithiol.

Following the fluorination of at least one disulfide or thiol group in the starting material, the fluorinated precursor is further reacted in order to introduce a labile group into the molecule, said group being capable of further reaction with another compound to facilitate introduction of the fluorinated moiety into a larger molecule such as a drug molecule. Said labile group may be introduced by treatment of the fluorinated precursor with any suitable reagent which is capable of introducing such a labile group into a vacant position on the aromatic or heterocyclic ring.

As previously observed, particularly suitable labile groups in the context comprise amino, bromo or nitro groups, all of which may be conveniently introduced into this fluorinated precursor. Thus, a nitro group may be introduced into the molecule by direct nitration; this group; may then optionally be reduced to provide the corresponding amino derivative. Alternatively, a bromo group may be substituted into the ring by direct bromination. This may, for example, be carried out by reacting the fluorinated precursor with bromine in the presence of elemental fluorine.

Specifically, by way of example, the preparation of (3-bromo-5-(trifluoromethyl)phenyl) sulfurpentafluoride has been achieved by the direct bromination of 3-(trifluoromethyl)phenyl) sulfurpentafluoride in the presence of elemental fluorine, and 3,5-bis(pentafluorosulfuryl) bromobenzene has been similarly obtained from 1,3-bis (pentafluorosulfuryl)benzene.

Both (3-bromo-5-(trifluoromethyl)phenyl) sulfurpentafluoride and 3,5-bis (pentafluorosulfuryl)bromobenzene find particular application as intermediates for the preparation of medicaments for the treatment of, for example, asthma and arthritis.

What is claimed is:

1. A polyfluorinated benzene compound having three ring substituents, at least one of which is a sulfurpentafluoride group, at least one of which is a labile group, and at least one of which is a trifluoromethyl group, wherein said compound is a derivative of benzene substituted in the 1-, 3-, and 5-positions.

2. A compound as defined in claim 1 which includes one or two sulfurpentafluoride groups.

3. A compound as defined in claim 1 wherein said labile group is an amino, bromo or intro group.

4. A compound as defined in claim 1 which includes a bromo group and a trifluoromethyl group.

5. A compound as defined in claim 1 which is selected from the group consisting of
(3-amino-5-(trifluoromethyl) phenyl)sulfurpentafluoride,
(3-bromo-5-(trifluoromethyl)phenyl)sulfurpentafluoride and (3-nitro-5-(trifluoromethyl)phenyl)sulfurpentafluoride.

6. A method for the preparation of a polyfluorinated benzene compound according to claim 1, said method comprising:
(a) treating a benzene compound having two ring substituents, at least one of which is a disulfide or thiol group, with fluorine; and
(b) introducing a labile group into said fluorinated precursor.

7. A method as defined in claim 6 wherein said treatment with fluorine comprises treatment with elemental fluorine.

8. A method as defined in claim 6 wherein said labile group is a bromo or nitro group, and said introduction is achieved by bromination or nitration of said fluorinated precursor.

9. A method as defined in claim 6 wherein said labile group is an amino group and said introduction is achieved by nitration of the fluorinated precursor and reduction of the nitro group.

10. A method as defined in claim 8 wherein said labile group is a bromo group and said bromination is carried out by treatment with bromine and elemental fluorine.

11. A method as defined in claim 6 wherein said polyfluorinated aromatic or heterocyclic compound is
(3-amino-5-trifluoromethyl)phenyl)sulfurpentafluoride,
(3-bromo-5-trifluoromethyl)phenyl)sulfurpentafluoride or
(3-nitro-5-(trifluoromethyl)phenyl)sulfurpentafluoride.

12. A medicament comprising a compound as defined in claim 1.

* * * * *